(12) United States Patent
Hansson

(10) Patent No.: US 7,931,653 B2
(45) Date of Patent: Apr. 26, 2011

(54) DEVICE AT FIXING MEANS FOR FIXATION OF BONE FRAGMENTS AT BONE FRACTURES

(76) Inventor: Henrik Hansson, Eriksberg (SE)

( * ) Notice: Subject to any disclaimer, the term of this patent is extended or adjusted under 35 U.S.C. 154(b) by 814 days.

(21) Appl. No.: 10/535,977

(22) PCT Filed: Dec. 1, 2003

(86) PCT No.: PCT/SE03/01845
§ 371 (c)(1),
(2), (4) Date: May 24, 2005

(87) PCT Pub. No.: WO2004/049963
PCT Pub. Date: Jun. 17, 2004

(65) Prior Publication Data
US 2006/0064098 A1 Mar. 23, 2006

(30) Foreign Application Priority Data
Dec. 4, 2002 (SE) ........................ 0203583

(51) Int. Cl.
*A61B 17/72* (2006.01)
(52) U.S. Cl. ........................................ 606/63
(58) Field of Classification Search ............. 606/62–68
See application file for complete search history.

(56) References Cited

U.S. PATENT DOCUMENTS

| | | | |
|---|---|---|---|
| 2,998,007 A | 8/1961 | Herzog | |
| 3,791,380 A * | 2/1974 | Dawidowski | 606/68 |
| 5,135,527 A * | 8/1992 | Ender | 606/62 |
| 5,281,225 A * | 1/1994 | Vicenzi | 606/62 |
| 5,810,820 A * | 9/1998 | Santori et al. | 606/63 |
| 5,971,968 A * | 10/1999 | Tu et al. | 604/264 |
| 6,554,833 B2 * | 4/2003 | Levy et al. | 606/63 |
| 6,783,530 B1 * | 8/2004 | Levy | 606/63 |
| 7,258,692 B2 * | 8/2007 | Thelen et al. | 606/62 |
| 2004/0049192 A1 * | 3/2004 | Shimizu | 606/62 |

FOREIGN PATENT DOCUMENTS

| | | |
|---|---|---|
| DE | 2 166 339 | 1/1974 |
| EP | 0 064 724 A2 | 11/1982 |
| WO | WO 95/31942 A1 | 11/1995 |
| WO | WO 2002/011632 A1 | 2/2002 |

* cited by examiner

*Primary Examiner* — Thomas C Barrett
*Assistant Examiner* — Michael J Araj
(74) *Attorney, Agent, or Firm* — Tarolli, Sundheim, Covell & Tummino LLP

(57) ABSTRACT

The present invention relates to a device at fixing means for fixation of bone fragments at bone fractures, the fixing means (1) preferably being a spike for fixation of bone fragments at trochantery hip fractures. The fixing means (1) comprises a sleeve (5) and a pin (7) which is insertable into the sleeve (5) and displaceable in the longitudinal direction thereof. The pin (7) has a rear part (8) and at least two front parts (9, 10) with bent points or tips. Front parts of the sleeve (5) have openings (13, 14) through which the front parts (9, 10) of the pin (7) can be forced. The front parts (9, 10) of the pin (7) have a successively increasing thickness in backwards direction towards the rear part (8) of the pin (7) such that said front parts (9, 10), when forced or driven out of the sleeve (5) through the openings (13, 14), are formed into arcuate parts, the points (11, 12) of which are curved in backwards direction or substantially backwards relative to a geometric centre line along the pin (7), and such that those portions of the front parts (9, 10) which after said outward driving of the front parts (9, 10) are situated at the sleeve (5), are thicker and thereby stronger than those portions of the front parts (9, 10) which grip into the bone material (3).

22 Claims, 2 Drawing Sheets

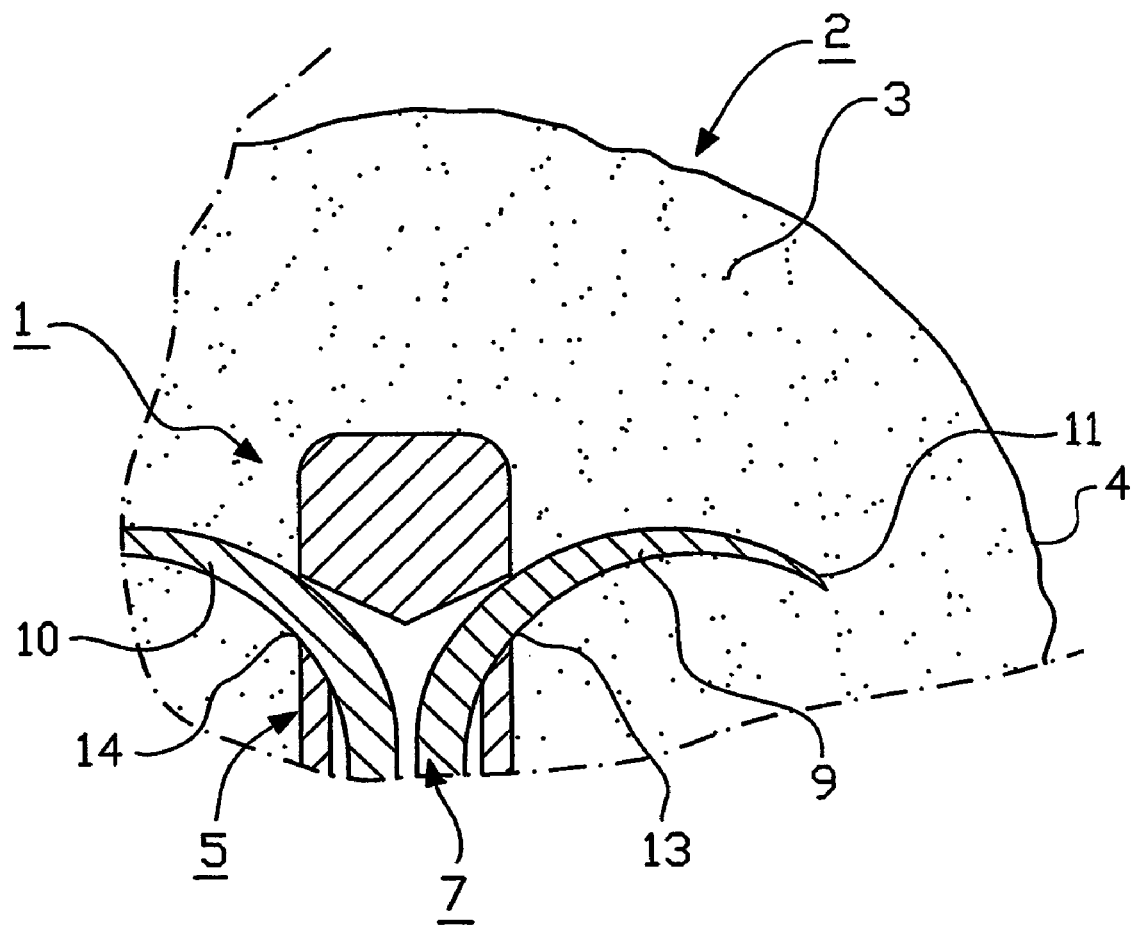

DEVICE AT FIXING MEANS FOR FIXATION OF BONE FRAGMENTS AT BONE FRACTURES

FIELD OF THE INVENTION

The present invention relates to a device at fixing means for fixation of bone fragments at bone fractures, said fixing means preferably being a spike for fixation of bone fragments at trochantery hip fractures. The fixing means comprises a sleeve and a pin which is insertable into the sleeve and displaceable in the longitudinal direction thereof. The pin has a rear part and at least two front parts. The front parts are provided with bent points or tips and front parts of the sleeve have openings through which the front parts of the pin can be forced.

BACKGROUND OF THE INVENTION

Fixing means for fixation of bone fragments at bone fractures are known from the publication WO 95/31942. This fixing means comprises a sleeve with two pins, the front parts of which can be forced out of the sleeve in opposite directions and into surrounding bone material. These front parts of the pins are of uniform thickness, which has resulted in that they when being forced out of the sleeve are formed into poorly arcuate and often even straight parts, particularly if the spike is made of a titanium alloy. Such forms of the parts being forced out are not optimum because there is a risk that they are forced out through joint surfaces of the bones in which they are provided, which is not acceptable.

SUMMARY OF THE INVENTION

The object of the present invention is to eliminate these problems and this is arrived at by providing the device defined above with the characterizing features of subsequent claim 1.

Since the two front parts of the pin, which can be pressed out of the sleeve, have a successively increasing thickness in backwards direction towards the rear parts of the pin, several essential advantages are obtained, namely a) that the two front parts of the pin being forced or pressed into the bone material, get an advantageous grip therein, b) that there will be no risk that the two parts being forced or pressed out, are pressed through outer heads of surrounding bone material, and c) that said two front parts become greater at the openings through which they extend than at those portions gripping into the bone material, whereby said portions better withstand forces applied thereto by the sleeve if e.g. the sleeve is pressed or pushed in forward direction.

BRIEF DESCRIPTION OF THE DRAWINGS

The invention will be further described below with reference to the accompanying drawings, in which:

FIG. 5 is a section through front parts of a fixing means which a device according to the invention gripping into a head of femur or thigh-bone head.

DESCRIPTION OF EXAMPLE EMBODIMENTS

Figure 1:
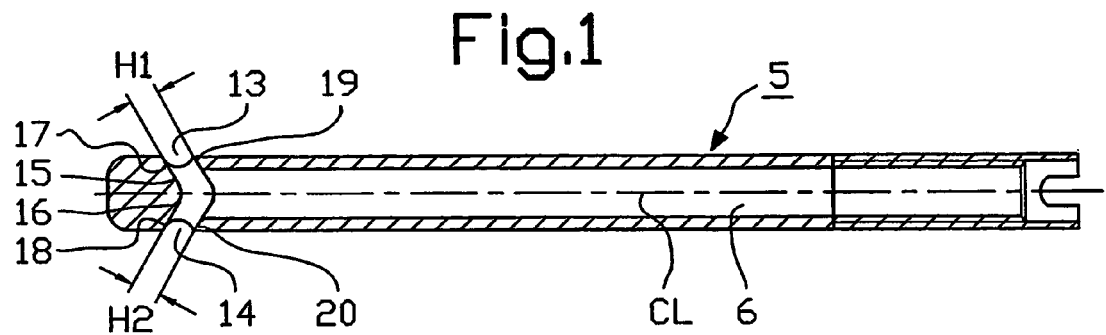
FIG. 1 is a longitudinal section through a sleeve forming part of the device according to the invention.
Figure 2:
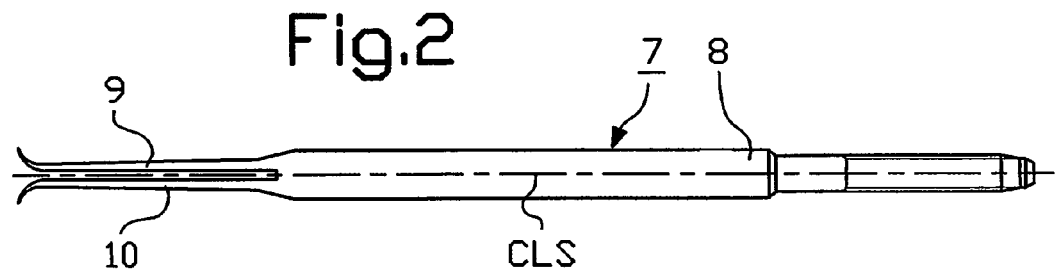
FIG. 2 is a side view of a pin which is insertable into the sleeve of FIG. 1.
Figure 3:
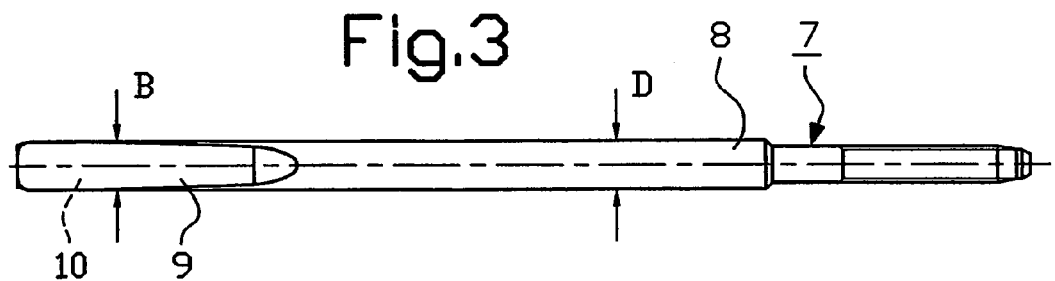
FIG. 3 is another side view of the pin of FIG. 2.
Figure 4:
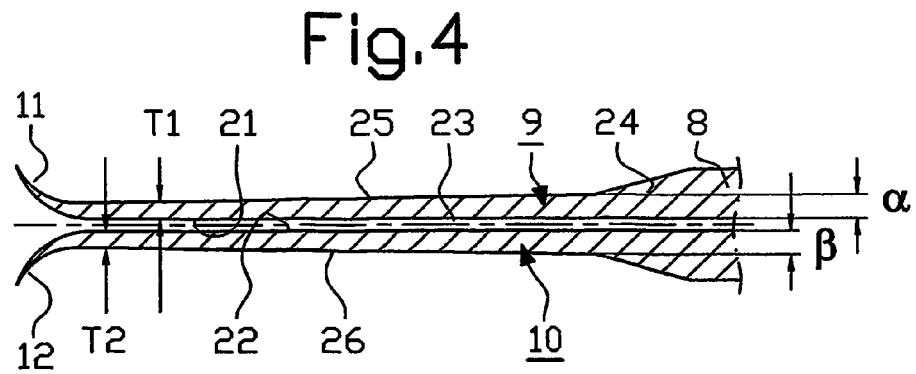
FIG. 4 is a longitudinal section through two front portions of the pin of FIGS. 2 and 3.

The fixing means 1 illustrated in the drawings is a collum or thigh-bone neck spike for fixation of bone fragments at trochantery hip fractures. In FIG. 5, front parts of this spike are shown located in the bone material 3 of the thigh-bone head 2 within the joint surfaces 4 of the thigh-bone head. The fixing means 1 has a sleeve 5 with a longitudinal space 6 which is open at the rear for insertion of a pin 7. The pin 7 is displaceable in the longitudinal direction of the sleeve 5 and has a rear part 8 and two front parts 9, 10 which extend from said rear part 8 in forward direction. Each front part 9, 10 has, at the front, a bent point or tip 11, 12 and these points 11, 12 are directed away from each other.

Front parts of the sleeve 5 have two openings 13, 14 which are located on opposite sides of said sleeve 5. One of the front parts 9 and 10 respectively, of the pin 7 can be forced out of the sleeve 5 through each opening 13 and 14 respectively, therein, by driving the pin 7 in forward direction relative to said sleeve 5. This driving of the pin 7 in forward direction relative to the sleeve 5 is carried through by means of driving or actuator instruments which may be of a prior art type and which are not further illustrated or described here.

At the front, the space 6 of the sleeve 5 ends with two guide surfaces 15, 16, which are directed from a geometric longitudinal centre line CL, extending along the space 6 of the sleeve 5, in a direction obliquely forward/outward to such a front edge 17 and 18 respectively, of each opening 13 and 14 respectively, which, relative to the sleeve 5, is situated in front of a rear edge 19 and 20 respectively, of each opening 13 and 14 respectively.

In a ready position (not shown) in which the pin 7 is inserted into the sleeve 5, one point 11 of said pin 7 is in engagement with the guide surface 15 or close thereto and the other point 12 is in engagement with the guide surface 16 or close thereto. When driving the pin 7 in forward direction relative to the sleeve 5, the guide surface 15 will guide said one front part 9 of the pin 7 out of the opening 13 and the guide surface 16 will guide said other front part 10 of the pin 7 out of the opening 14.

The front parts 9, 10 may have rectangular or substantially rectangular cross sections and inner surfaces 21 and 22 respectively, facing each other, of the front parts 9, 10 may be located close to each other, i.e. there may be a narrow slit 23 therebetween, and this slit 23 extend from the points 11, 12 to a transfer part 24 through which the rear part 8 transforms into the front parts 9, 10. The front parts 9 and 10 respectively, are preferably designed as straight parts or substantially straight parts and said inner surfaces 21, 22 are preferably rectilinear or substantially rectilinear and preferably also parallel or substantially parallel relative to each other as well as to a geometric centre line CLS, extending in the longitudinal direction of the pin 7. Outer surfaces 25 and 26 respectively, facing away from each other, of the front parts 9, 10 are preferably also rectilinear or substantially rectilinear.

Each front part 9 and 10 respectively, has, in a direction backwards from its point or tip 11 and 12 respectively, towards the rear part 8, a successively increasing thickness T1 and T2 respectively. The thickness T1 and T2 respectively, may increase in backwards direction such that the angle $\alpha$ and $\beta$ respectively, between the inner surface 21 and 22 respectively, and the outer surface 25 and 26 respectively, of each front part 9 and 10 respectively, is between 0.5° and 1°. A preferred angle $\alpha$ and $\beta$ may be 0.75° or close to 0.75°. The successively increasing thickness T1 and T2 respectively, of the front parts 9 and 10 respectively, permits that those portions of said front parts 9, 10 situated in the openings 13 and 14 respectively, i.e. the portions cooperating with the sleeve 5, are thicker and thereby stronger than those portions of said front parts 9, 10 gripping into the bone material 3. This means that if e.g. the sleeve 5 is loaded in forward direction relative to the pin 7, which might be the case when the fixing means 1 is provided in the thigh bone, strong portions of the front parts 9, 10 may withstand these loads better than if said front parts 9, 10 have a uniform thickness. The thicker the front parts 9, 10 are, the more they are bent in backwards direction when they pass the edges 19, 20 of the openings 13, 14. Hereby, the front parts 9, 10 are formed into arcuate parts, the points 11, 12 of which get curved backwards or substantially backwards relative to the longitudinal, geometric centre line CLS of the pin 7. Hereby, it is achieved that the front parts 9, 10 attach advantageously to the bone material 3 and the risk of that they penetrate out of the joint surfaces 4 of the thigh-bone head 2 or similar is eliminated.

The openings 13, 14 preferably have a height H1 and H2 respectively, between their front and rear edges 17, 19 and 18, 20 respectively, which only somewhat exceeds the thickness of those portions of the front parts 9, 10 which after expelling or outward driving of said front parts 9, 10 are situated in the openings 13, 14. Hereby, it is achieved, inter alia, that the cooperation between said portions and the sleeve 5 becomes stable and the consumption of forces affecting the front parts 9, 10 favourable.

If the fixing means 1 is used for fixation of trochantery hip fractures, the thickness T1 and T2 respectively, of the front parts 9, 10 may increase successively in such manner in backwards direction that said front parts 9, 10 during outwards pressing are formed into arcuate parts, the points 11, 12 of which are situated within a joint surface 4 of the thigh-bone head 2 and follow or substantially follow the curved shape of said joint surface 4.

The front parts 9 and 10 respectively, have preferably the same width along their entire or substantially entire length and this width is preferably only somewhat less than the width of the opening 13 and 14 respectively. The width B of the front parts 9, 10 corresponds preferably with an outer diameter D of the rear part 8 or corresponds substantially with said diameter D.

The points 11, 12 of the front parts 9, 10 may also have a successively increasing thickness in backwards direction.

The sleeve 5 is preferably cylindrical and the rear part 8 of the pin 7 has preferably a circular outer diameter D which at least partially is adapted to the inner diameter of the sleeve 5. The rear parts of the pin 7 are at the back designed for connection to driving and/or retraction instruments.

The invention is not limited to what is described above and illustrated in the drawings, but may vary within the scope of the subsequent claims. As embodiments not described it can be mentioned that the pin 7 may have more than two front parts 9, 10 and if that is the case, the sleeve 5 may have more than two openings 13, 14. The fixing means 1 may be used for fixing bone fragments at fractures of other bones in the body than thigh-bone fractures. The sleeve 5 and/or the pin 7 may be made of stainless steel or titanium alloy.

The invention claimed is:

1. Device at fixing means for fixation of bone fragments at bone fractures,
    said fixing means (1) preferably being a spike for fixation of bone fragments at trochantery hip fractures,
    wherein the fixing means (1) comprises a sleeve (5) and a pin (7) which is insertable into the sleeve (5) and displaceable in the longitudinal direction thereof, the pin (7) having a geometric centre line (CLS),
    wherein the pin (7) has a rear part (8) and at least two front parts (9, 10) with bent points or tips (11, 12), and
    wherein front parts of the sleeve (5) have openings (13, 14) through which the front parts (9, 10) of the pin (7) can be forced,
    characterized in
    that the front parts (9, 10) of the pin (7) have a successively increasing thickness (T1 and T2 respectively) in backwards direction to the rear part (8) of the pin (7) such that said front parts (9, 10), when forced or driven out of the sleeve (5) through the openings (13, 14), are formed into arcuate parts, the points (11, 12) of which are curved in a backwards direction such that each front part (9, 10) intersects an axis extending through the openings (13, 14) and perpendicular to the geometric centre line (CLS) twice, and such that those portions of the front parts (9, 10) which after said outward driving of said front parts (9, 10) are situated at the sleeve (5), are thicker and thereby stronger than those portions of said front parts (9, 10) which grip into the bone material (3).

2. Device according to claim 1, characterized in that the openings (13, 14) have a height (H1 and H2 respectively) between a front edge and a rear edge (17, 19 and 18, respectively) thereof which only somewhat exceeds the thickness of those portions of the front parts (9, 10) which after said outward driving of said front parts (9, 10) are situated in the openings (13, 14).

3. Device according to claim 2, wherein the fixing means (1) is provided in a thigh bone and the front parts (9, 10) of the pin (7) grip into the thigh-bone head (2), characterized in that the thickness (T1 and T2 respectively) of the front parts (9, 10) increases successively in backwards direction towards the rear part (8) of the pin (7) such that the thicker the front parts (9, 10) are when they pass the rear edges (19, 20) of the openings (13, 14), the more they are bent in backwards direction, whereby said front parts (9, 10) during said outward driving thereof are formed into arcuate parts, the points (11, 12) of which are situated within joint surfaces (4) of the thigh-bone head (2) and follow or substantially follow the curved shape of said joint surfaces (4).

4. Device according to claim 1, characterized in
    that inner surfaces (21, 22) of the front parts (9, 10), facing each other, are rectilinear or substantially rectilinear,
    that outer surfaces (25, 26) of the front parts (9, 10), facing away from each other, are rectilinear or substantially rectilinear, and
    that the angle ($\alpha$ and $\beta$ respectively) between the inner surfaces (21, 22) and the outer surfaces (25, 26) is 0.5°-1° and preferably 0.75° or close to this angle.

5. Device according to claim 4, characterized in that the inner surfaces (21, 22) of the front parts (9, 10) are provided in parallel or substantially in parallel with each other and in parallel or substantially in parallel with the geometric centre line (CLS) extending along the pin (7).

6. Device according to claim 1, characterized in that the front parts (9, 10) have a rectangular or substantially rectangular shape.

7. Device according to claim 1, characterized in that the front parts (9, 10) have the same or substantially the same width (B) along its entire length or substantially entire length and that this width (B) is only somewhat less than the width of the opening (13 and 14 respectively).

8. Device according to claim 1, characterized in that the front parts (9, 10) have the same width (B) or substantially the same width (B) as an outer diameter (D) of the rear part (8) of the pin (7).

9. Device according to claim 1, characterized in that the front parts (9, 10) are straight or substantially straight parts with bent points or tips (11, 12).

10. Device according to claim 1, characterized in that the front parts (9, 10) have bent points or tips (11, 12) with successively increasing thickness in backwards direction.

11. Device according to claim 1, characterized in that the sleeve (5) and the pin (7) are made of stainless steel.

12. Device according to claim 1, characterized in that the sleeve (5) and the pin (7) are made of titanium alloy.

13. The apparatus of claim 1, wherein each front part curves over to one side of the axis that extends through the openings and perpendicular to the geometric centre line and then back over to the other side of the axis.

14. An apparatus for fixating bone fragments at trochantery hip fractures, the apparatus comprising:
    a sleeve; and
    a pin having a geometric center line and being insertable into the sleeve and longitudinally displaceable relative to the sleeve, the pin having a plurality of front parts and a rear part, each of the plurality of front parts having a bent tip with a first thickness, the rear part having a second thickness greater than the first thickness, the front parts increasing in thickness to the rear part, the sleeve having openings through which the front parts of the pin are forced, the front parts of the pin being formed into arcuate parts and the tips of the pin being curved in a backwards direction towards the rear part of the pin such that each front part intersects an axis extending through the openings and perpendicular to the geometric center line twice when the tips of the pin grip the bone fragments and the front parts are forced through the openings in the sleeve, portions of the front parts of the pin cooperating with the openings in the sleeve after the front parts are forced through the openings, the portions being thicker and thereby stronger than those portions of the front parts that grip the bone fragments.

15. The apparatus of claim 14, wherein a front edge and a rear edge of each opening define a height, the height only somewhat exceeding the thickness of the portions of the front parts which are situated in the openings after the front parts are forced through the openings.

16. The apparatus of claim 15, wherein the tips of the front parts bend further in the backwards direction as the thickness of the front part passing by the rear edge of the opening increases from the first thickness to the second thickness, the tips of the front parts being situated within joint surfaces of a thigh-bone head and following the curved shape of the joint surfaces when the front parts are forced through the openings in the sleeve.

17. The apparatus of claim 14, wherein
    inner surfaces of the front parts face each other, the inner surfaces being rectilinear or substantially rectilinear,
    outer surfaces of the front parts face away from each other, the outer surfaces being rectilinear or substantially rectilinear, and
    the angle between the inner surfaces and the outer surfaces is 0.5°-1°.

18. The apparatus of claim 17, wherein the inner surfaces of the front parts are substantially parallel to both one another and a center line of the pin.

19. The apparatus of claim 14, wherein the front parts have a rectangular or substantially rectangular shape.

20. The apparatus of claim 14, wherein the front parts have substantially the same width along its length, the width being somewhat less than the width of the opening.

21. The apparatus of claim 14, wherein the front parts are substantially straight with bent points or tips before the front parts are forced through the openings.

22. The apparatus of claim 14, wherein each front part curves over to one side of the axis that extends through the openings and perpendicular to the geometric centre line and then back over to the other side of the axis.

* * * * *